(12) United States Patent
Humes et al.

(10) Patent No.: US 8,985,560 B2
(45) Date of Patent: Mar. 24, 2015

(54) OXYGEN HUMIDIFIER

(75) Inventors: Zachary E. Humes, North Logan, UT (US); Nathan D. McCulloch, Logan, UT (US); David K. Webb, Smithfield, UT (US); Ryan A. Mawson, Logan, UT (US)

(73) Assignee: FLO EZ Technologies, Logan, UT (US)

( * ) Notice: Subject to any disclaimer, the term of this patent is extended or adjusted under 35 U.S.C. 154(b) by 417 days.

(21) Appl. No.: 13/489,178

(22) Filed: Jun. 5, 2012

(65) Prior Publication Data

US 2012/0312298 A1 Dec. 13, 2012

Related U.S. Application Data

(60) Provisional application No. 61/494,959, filed on Jun. 9, 2011.

(51) Int. Cl.
*B01F 3/04* (2006.01)
*B01D 47/02* (2006.01)
*A61M 16/10* (2006.01)
*A61M 15/00* (2006.01)
*A61M 16/16* (2006.01)
*A61M 16/20* (2006.01)
*A61M 16/06* (2006.01)

(52) U.S. Cl.
CPC .............. *A61M 16/16* (2013.01); *A61M 16/10* (2013.01); *A61M 16/208* (2013.01); *A61M 2202/0208* (2013.01); *A61M 2205/183* (2013.01); *A61M 2205/3382* (2013.01); *A61M 2205/3386* (2013.01); *A61M 2205/581* (2013.01); *A61M 2205/584* (2013.01); *A61M 16/0672* (2014.02); *A61M 16/209* (2014.02)

USPC ................................... 261/121.1; 128/203.15

(58) Field of Classification Search
USPC .............. 128/23.12, 203.16, 204.18, 205.11, 128/205.22, 200.24; 261/121.1, 122.2, 124
See application file for complete search history.

(56) References Cited

U.S. PATENT DOCUMENTS

| | | | |
|---|---|---|---|
| 1,098,623 A | 6/1914 | Haeusler | |
| 2,111,654 A | 3/1938 | Wires | |
| 2,902,269 A * | 9/1959 | Eichelman | .................... 261/124 |
| 3,757,082 A | 9/1973 | Goicoechea | |
| 3,864,440 A | 2/1975 | Giocoechea | |
| D234,641 S | 3/1975 | King et al. | |
| 3,982,095 A | 9/1976 | Robinson | |
| D263,337 S | 3/1982 | Hart et al. | |
| 4,367,182 A * | 1/1983 | Kienholz | ...................... 261/124 |
| 4,767,576 A * | 8/1988 | Bagwell | ......................... 261/16 |
| 5,015,394 A * | 5/1991 | McEllhenney et al. | ........ 210/744 |
| 5,190,648 A * | 3/1993 | Ramsauer | ..................... 210/695 |
| 5,378,480 A * | 1/1995 | Carieri | ............................ 426/67 |
| 5,588,423 A | 12/1996 | Smith | |

(Continued)

*Primary Examiner* — Kristen Matter
(74) *Attorney, Agent, or Firm* — Kunzler Law Group, PC

(57) ABSTRACT

According to one specific embodiment, an oxygen humidifier includes a container that defines an interior space. The oxygen humidifier also includes a top portion that is permanently coupled to the container. The top portion includes an opening for accessing the interior space of the container. The humidifier further includes a lid portion that is movably coupled to the top portion. The lid portion is configured to move between a closed configuration and an open configuration. In the closed configuration, the lid portion seals the opening, and in the open configuration, the lid portion allows access to the interior space through the opening. The oxygen humidifier additionally includes an oxygen diffuser positioned within the interior space.

19 Claims, 12 Drawing Sheets

(56) References Cited

U.S. PATENT DOCUMENTS

| | | | |
|---|---|---|---|
| 5,733,447 A * | 3/1998 | Makar | 210/220 |
| 6,202,991 B1 | 3/2001 | Coniglio et al. | |
| 6,786,475 B2 | 9/2004 | Salter et al. | |
| 2011/0068113 A1 * | 3/2011 | Kim | 220/713 |

* cited by examiner

OXYGEN HUMIDIFIER

CROSS-REFERENCE TO RELATED APPLICATION

This application claims the benefit of U.S. Provisional Patent Application No. 61/494,959, filed Jun. 9, 2011, which is incorporated herein by reference.

FIELD

This disclosure relates generally to medical devices, and more particularly to oxygen humidifiers.

BACKGROUND

Oxygen humidifiers for humidifying an oxygen supply prior to inhalation by a user are known in the art. Such oxygen humidifiers are useful, and often necessary, for users with sensitive lungs that require long-term or short-term assisted breathing. The oxygen humidifiers humidify a flow of dry oxygen from an oxygen source and supply a stream of humidified oxygen to a user.

Typical oxygen humidifiers include a container for storing water and a cap or lid that covers the container. An oxygen inlet line provides dry oxygen with a low percent humidity through a port in the cap. The dry oxygen is introduced into the fluid through an outlet positioned within the water. As the dry oxygen is released into the water and filters up to the surface of the water, water molecules diffuse into the dry oxygen. Accordingly, the oxygen emitting from the water contains more water molecules or moisture than the dry oxygen initially released into the water. Oxygen humidifiers also include an oxygen outlet line that receives humidified oxygen from the container through another port in the cap. The oxygen outlet line terminates at a breathing apparatus that is usable by a user to access the humidified oxygen.

Because water molecules in the container are being added to the oxygen being released to a user for inhalation, the amount of water stored in the container is depleted over time. Therefore, from time-to-time, water must be added to the container to replenish the water lost during use of the oxygen humidifier. To add water to the container, the cap or lid of conventional oxygen humidifiers is designed to be removable. For example, the cap and container of conventional humidifiers include respective mating threads. The mating threads are rotatably engageable with each other such that rotation of the cap in one direction relative to the container loosens the cap from the container and rotation of the cap in an opposite direction relative to the container tightens the cap against the container. Although threaded connections of this type are common, cross-threading between the threads of the cap and container (or mis-threading the threads of the cap with the threads of the container) is common. When cross-threading occurs, the seal between the cap and container is broken and the oxygen humidifier fails to operate properly. Further, cross-threading is not easily detectable. Moreover, because the cap is completely removed from the container, the cap is prone to misplacement and being lost, as well as contamination. Additionally, unscrewing a lid from a container and screwing a lid onto a container requires a relatively high level of dexterity and manual involvement (e.g., the use of multiple fingers of at least one hand).

Additionally, conventional oxygen humidifiers use various techniques and devices to release dry oxygen into the water. However, such techniques and devices each suffer from various shortcomings. For example, most conventional oxygen humidifiers fail to distribute the released oxygen into the water widely enough, uniformly enough, and away from the sides of the container where oxygen tends to accumulate.

SUMMARY

The subject matter of the present application has been developed in response to the present state of the art, and in particular, in response to the problems and needs in oxygen humidifier art that have not yet been fully solved by currently available oxygen humidifiers. Accordingly, the subject matter of the present application has been developed to provide an oxygen humidifier, and associated system and method, for humidifying oxygen in breathing-assistance applications that overcomes many of the shortcomings of the prior art. For example, in some embodiments, an oxygen humidifier is disclosed that allows access to the container for adding water without requiring removal of an entire cap. Such embodiments employ a pivotable hatch coupled to a cap that is permanently fixed to the container. In this manner, the possibility of cross-threading the cap and container, losing or contaminating a removed cap, and difficult or tedious engagement and disengagement between the cap and container is eliminated. Moreover, in certain embodiments, the oxygen humidifier disclosed herein includes an oxygen diffuser positioned deep within the container away from the sidewall of the container. The oxygen diffuser has an patterned arrangement of a plurality of outlet channels for widely and uniformly dispersing oxygen into the water away from the sidewall.

According to one specific embodiment, an oxygen humidifier includes a container that defines an interior space. The oxygen humidifier also includes a top portion that is permanently coupled to the container. The top portion includes an opening for accessing the interior space of the container. The humidifier further includes a lid portion that is pivotally coupled to the top portion. The lid portion is configured to move (e.g., pivot) between a closed configuration and an open configuration. In the closed configuration, the lid portion seals the opening, and in the open configuration, the lid portion allows access to the interior space through the opening. The oxygen humidifier additionally includes an oxygen diffuser positioned within the interior space.

In some implementations, the humidifier further includes an oxygen inlet port that is formed in the top portion and a fluid conduit that is fluidly connected with the oxygen inlet port. The fluid conduit extends into the interior area of the container. The diffuser can be fluidly coupled with an end of the fluid conduit. The diffuser can be configured to diffuse an oxygen flow into a liquid retained within the container. In certain implementations, the fluid conduit and diffuser are positioned off-center within the interior of the container relative to a central axis of the container. The humidifier can also include an oxygen outlet port that is formed in the top portion.

In certain implementations, the humidifier includes a pressure release valve that is coupled with the top portion. The pressure release valve is configured to provide at least one of a visual and an aural notification when pressure inside the container has reached a predetermined pressure. The predetermined pressure can be in the range of between about 2 and 20 psi.

The lid portion can be rotatably coupled to the top portion with the lid portion being configured to rotate between the closed configuration and the open configuration. According to some implementations, the humidifier includes a lever that is coupled to and extends outward from the lid portion. A flange portion of the lever extends outwardly beyond an outer periphery of the opening. The flange portion of the lever can contact an outer surface of the top portion when the lid portion has moved or pivoted to the open configuration to prevent further movement or pivoting of the lid portion in an opening direction. The lid portion can be movable or pivotable by engaging the flange portion of the lever. In the open configuration, a substantial portion of the lever can be positioned within the interior space of the container.

In certain implementations, the diffuser is substantially spherical shaped and includes a plurality of openings through which oxygen is diffusible. Each of the plurality of openings open in directions substantially non-perpendicular relative to a sidewall of the container (which in some embodiments is parallel to a central axis of the container).

According to some implementations, the lid portion is releasably retained in the closed configuration via an interference fit between the lid portion and the top portion. The top portion can include a lip that defines the opening where the lip is inwardly angled relative to a center of the opening. The lid portion can include a ridge where an outer periphery of the ridge is greater than an inner periphery of the lip. In the same or other implementations, the lid portion can be releasably retained in the closed configuration via a detent mechanism. In yet the same or other implementations, the lid portion and/or the top portion includes a flexible gasket such that in the closed configuration the flexible gasket seals the opening. The lid portion can include a lip that defines an area greater than an area of the opening. The lip is contactable with an interior surface of the top portion to prevent upward rotation of the lid portion relative to the top portion beyond a position associated with the closed configuration.

The lid portion can be releasably retained in the open configuration via engagement between a cam element coupled to the lid portion and a latch element coupled to the top portion.

In yet another embodiment, an oxygen humidifier includes a container that defines an interior space for storing a fluid. The container includes an open end. The humidifier also includes a top portion that is coupled to the open end. The top portion includes an opening that is smaller than the open end of the container. The interior space is accessible through the opening in the top portion and the top portion further includes an oxygen inlet port and an oxygen outlet port. The lid portion is rotatably coupled to the top portion. The lid portion includes a lid and a lever coupled to the lid. The lid seals the opening via an interference fit in a closed position and is positioned within the interior space of the container to allow access to the interior space through the opening in the top portion in an open position. The lid is rotatable between the closed and open positions via actuation of the lever.

According to another embodiment, a method for humidifying oxygen includes directing dry oxygen into an oxygen humidifier. The oxygen humidifier includes a container and a top portion coupled to an open end of the container. The top portion includes an opening through which an interior of the container is accessible. The top portion also includes a lid that is sealingly engageable with the opening where the lid includes a handle that extends from the lid. The method additionally includes rotating the lid in a first direction to position the lid out of sealing engagement with the opening (and in some implementations within the container) via actuation of the handle. Further, the method includes preventing rotation of the lid in the first direction beyond a fully open position via contact between the handle and the top portion. Moreover, with the lid positioned out of sealing engagement with the opening, the method includes passing a fluid through the opening and into the retainer. The method also includes rotating the lid in a second direction opposite the first direction to position the lid into sealing engagement with the opening via actuation of the handle, and directing humidified oxygen from the oxygen humidifier.

The described features, structures, advantages, and/or characteristics of the subject matter of the present disclosure may be combined in any suitable manner in one or more embodiments and/or implementations. In the following description, numerous specific details are provided to impart a thorough understanding of embodiments of the subject matter of the present disclosure. One skilled in the relevant art will recognize that the subject matter of the present disclosure may be practiced without one or more of the specific features, details, components, materials, and/or methods of a particular embodiment or implementation. In other instances, additional features and advantages may be recognized in certain embodiments and/or implementations that may not be present in all embodiments or implementations. Further, in some instances, well-known structures, materials, or operations are not shown or described in detail to avoid obscuring aspects of the subject matter of the present disclosure. The features and advantages of the subject matter of the present disclosure will become more fully apparent from the following description and appended claims, or may be learned by the practice of the subject matter as set forth hereinafter.

BRIEF DESCRIPTION OF THE DRAWINGS

In order that the advantages of the subject matter may be more readily understood, a more particular description of the subject matter briefly described above will be rendered by reference to specific embodiments that are illustrated in the appended drawings. Understanding that these drawings depict only typical embodiments of the subject matter and are not therefore to be considered to be limiting of its scope, the subject matter will be described and explained with additional specificity and detail through the use of the drawings, in which.

DETAILED DESCRIPTION

Reference throughout this specification to "one embodiment," "an embodiment," or similar language means that a particular feature, structure, or characteristic described in connection with the embodiment is included in at least one embodiment of the present disclosure. Appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the present disclosure, however, absent an express correlation to indicate otherwise, an implementation may be associated with one or more embodiments.

Figure 1:
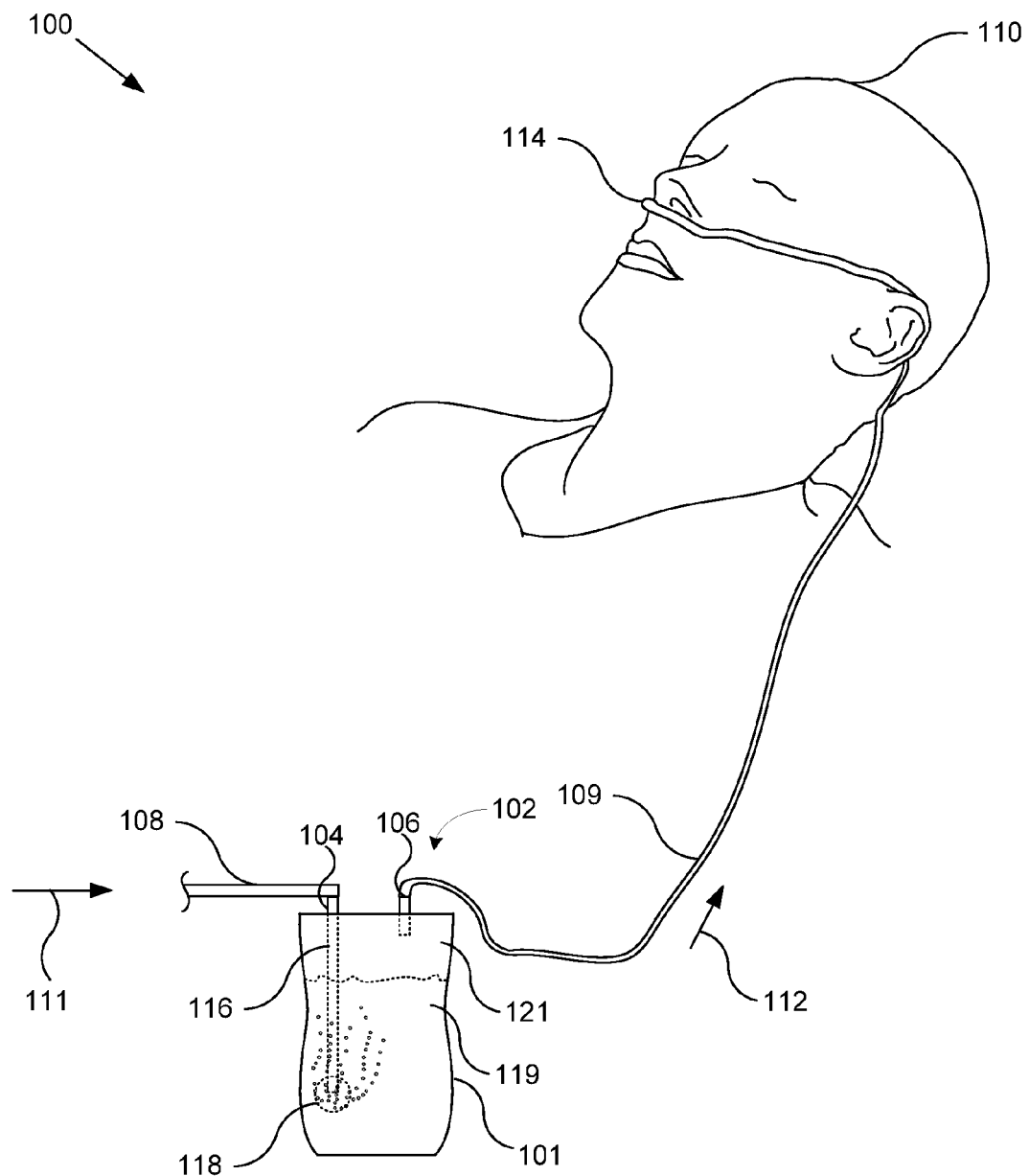
FIG. 1 is a representation of an oxygen supply system according to one embodiment.

Referring to FIG. 1, according to one embodiment, an oxygen supply system 100 includes an oxygen bubble humidifier 102. The bubble humidifier (hereinafter "humidifier") 102, as depicted, includes a fluid inlet port 104 and fluid outlet port 106. Connected to the inlet and outlet ports 104, 106 are respective inflow and outflow tubes 108, 109 that transport a fluid (e.g., oxygen) into and out of the humidifier 102, respectively. As used herein, the term "fluid" refers to a substance that has no fixed shape and yields easily to external pressure (e.g., is compressible). For example, a fluid can be a gas. As used herein, the term "exterior surface" or "outer surface" refers to a surface on the outside of the humidifier 102. Likewise, the term "interior surface" or "inner surface" refers to a surface on the inside of the humidifier 102.

The humidifier 102 provides a manner for humidifying a respiratory gas for a patient 110. In patients 110 with sensitive lungs, or in patients 110 that will receive long-term assisted breathing, dry oxygen can dry out mucous membranes, cause pulmonic infections, and damage lung tissue. The humidifier 102 humidifies the flow of dry oxygen entering the humidifier via the fluid inlet port 104 (see, e.g., directional arrow 111) to produce humidified oxygen, which subsequently exits the humidifier via the fluid outlet port 106 (see, e.g., directional arrow 112). In certain implementations, the humidifier 102 is used in high flow rate applications, such as breathing through a mask or a nasal cannula 114. The inflow tube 108 is in fluid receiving communication with a fluid source (e.g., an oxygen tube). A portion of the outflow tube 109 connects the humidifier 102 with the nasal cannula 114, or other oxygen delivery device, through which humidified oxygen is delivered directly to the patient 110.

In the illustrated embodiment, the humidifier 102 includes a fluid conduit 116 and a container 101 for storing a humidifying liquid 119. The fluid conduit 116 is positioned within the container 101 and disposed between the fluid inlet port 104 and a diffuser 118. In one implementation, the fluid conduit 116 and diffuser 118 are not coaxial with a central axis of the container (i.e., the fluid conduit and diffuser can be off-center relative to the central axis of the container). However, in some implementations, the fluid conduit 116 and diffuser 118 can be centered within the interior of the container or coaxial with a central axis of the container. Generally, the fluid conduit 116 directs incoming dry oxygen gas from the fluid inlet port 104 to the diffuser 118, which is positioned deep inside the container 101 at a location so as to be submerged by a minimum operating amount of the liquid 119 when stored within the container. The liquid 119, in one example, is substantially purified water. The diffuser 118 may be spherical and include a plurality of radially spaced outlets or channel for a broad and uniform distribution of oxygen into the liquid 119. The diffuser 118 will be discussed in greater detail below with reference to FIG. 8.

Generally, in operation, dry oxygen 111 is flowed from an oxygen source, through the inflow tube 108, the inlet port 104, the fluid conduit 116, and finally out into the liquid 119 via the diffuser 118. The dry oxygen is then humidified or moisturized as it "bubbles" upward through the liquid 119 inside the container 101. The humidified oxygen 121 accumulates within a space within the container 101 above the liquid 119. The accumulated humidified oxygen 121 then exits the container 101 through the outlet port 106 and flows 112 to the patient 110 via the outflow tube 109 and oxygen delivery device (e.g., the nasal cannula 114). The inlet port 104, fluid conduit 116, and diffuser 118, in certain embodiments, are laterally or radially offset from a longitudinal central axis of the container 101. In other words, the position of the inlet port 104, fluid conduit 116, and diffuser 118 can be off-center relative to the container 101. In some embodiments, the outlet port 106 also is off-center relative to a central axis of the container 101.

Figure 2:
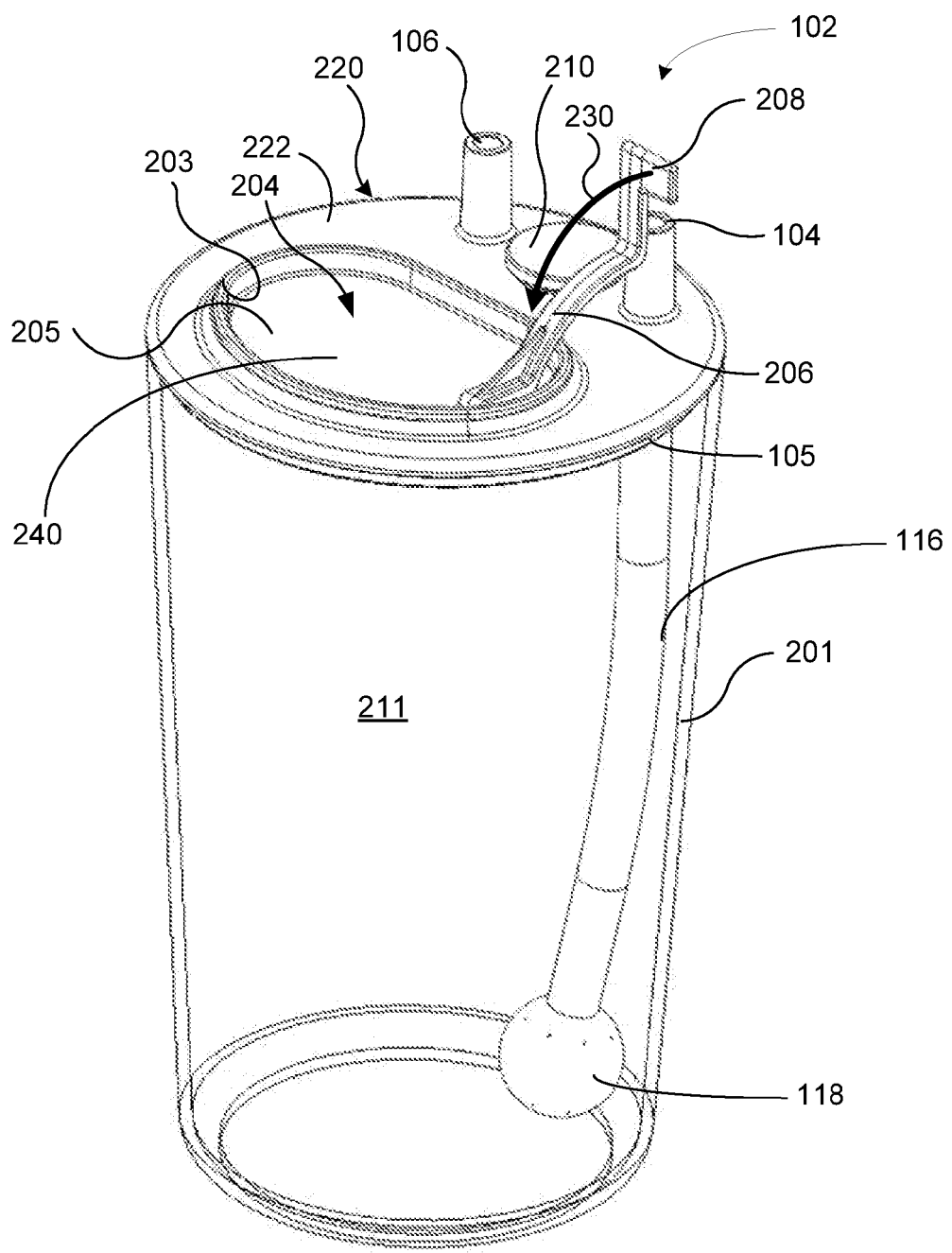
FIG. 2 is a top perspective view of an oxygen humidifier shown with a transparent container and a lid portion in a closed configuration according to one embodiment.
Figure 3:
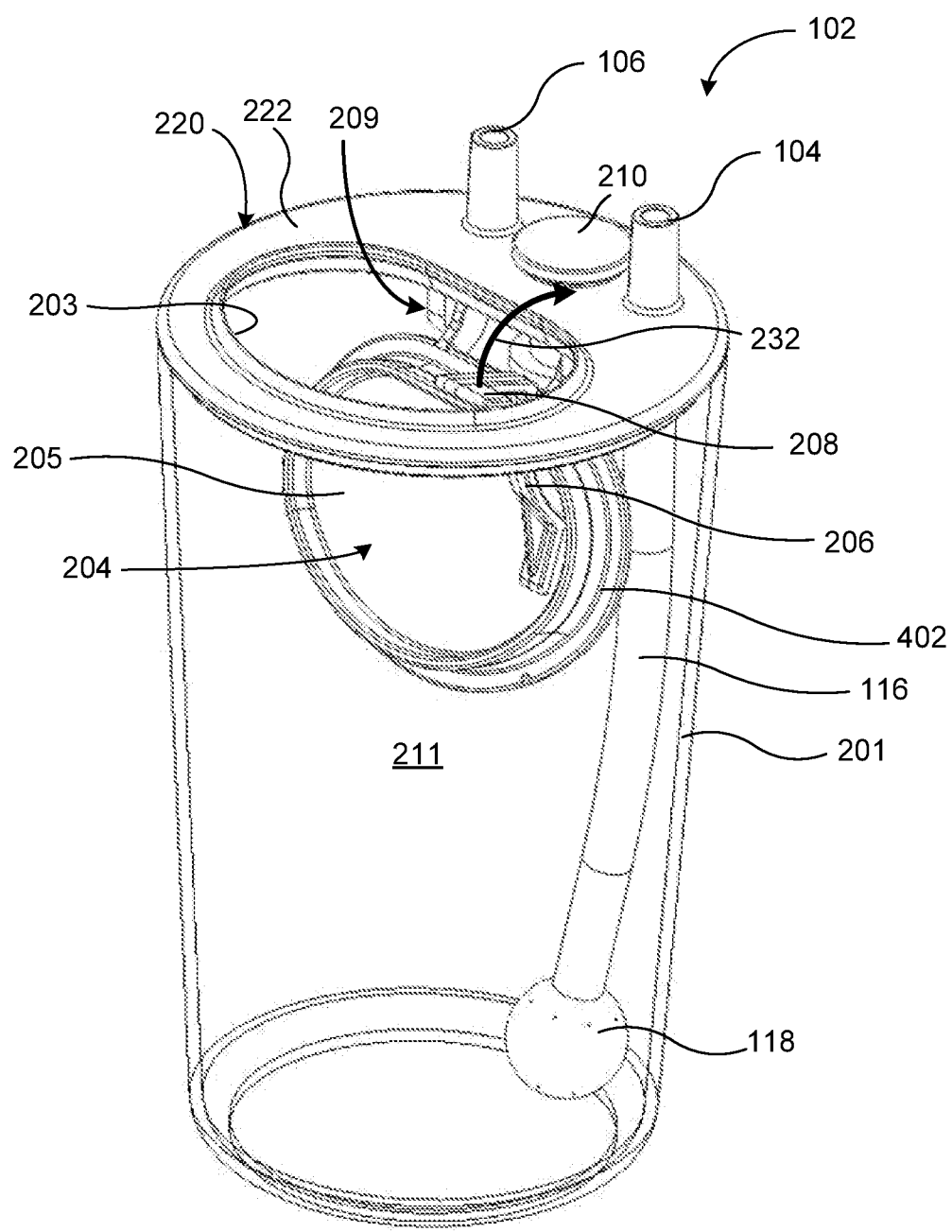
FIG. 3 is a top perspective view of the oxygen humidifier of FIG. 2 but shown with the lid portion in an open configuration.
Figure 4:
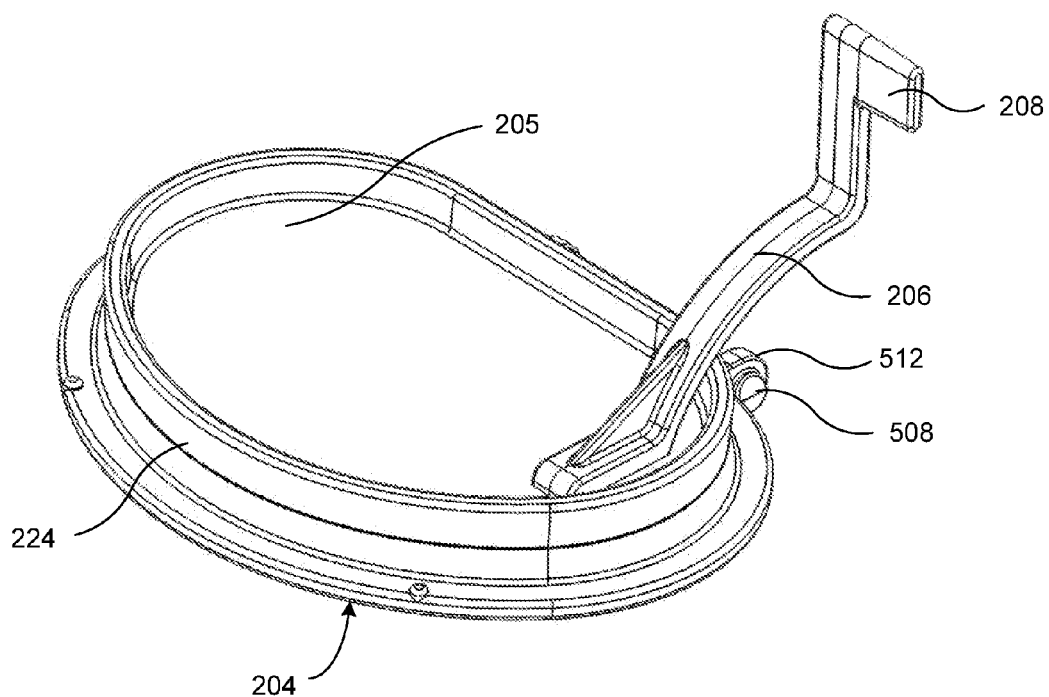
FIG. 4 is a perspective view of a lid portion according to one embodiment.

Referring to FIGS. 2 and 3, one embodiment of the humidifier 102 includes a container or body 201 for holding a quantity of the liquid 119, such as water. The body 201 in FIGS. 2 and 3 is depicted as being transparent to show the fluid conduit 116 and diffuser 118 in more detail as will be explained in more detail below. However, in some embodiments, the body 201 can be only partially transparent and even opaque if desired. The body 201 includes a single open end 105. Coupled to the open end 105 of the body 201 is a top portion 220. The top portion 220 is sized to encompass the entire open end 105 of the body 201, and configured to form a seal with the body. In one implementation, an outer periphery (e.g., circumference) of the open end 105 is substantially equal to the outer periphery (e.g., circumference) of the top portion 220. In other implementations, the outer periphery of the top portion 220 is larger than the outer periphery of the open end 105.

In one embodiment, the top portion 220 is formed separately from and permanently coupled with the body 201 of the humidifier 102. The separately formed top portion 220 may be permanently coupled with the body 201 via any of various techniques, such as plastic welded, heat sealed, or adhered using an adhesive. Moreover, the top portion 220 can be coupled to the body 201 of the humidifier with a non-threaded connection. In this manner, the top portion 220 is not removable from the body 201 without damaging either the top portion 220 or body 201. Alternatively, in some embodiments, the top portion 220 may be integrally formed (e.g., coupled) with the body 201 of the humidifier 102 to form a monolithic one-piece construction with the body. Whether the top portion 220 is permanently coupled or integrally formed with the body 201, such embodiments beneficially eliminate the problem of cross-threading between removable lids and containers commonly associated with conventional oxygen humidifiers.

Alternatively, although less desirable, the top portion 220 can be removably coupled with the body 220 in some embodiments. As will be explained in more detail below, because water can be added to the body 220 via a pivotable lid portion 204 of the top portion 220 in such embodiments, the entire top portion need not be removed to add water. Accordingly, because the top portion 220 need only be properly threadably connected to the body 201 a first time (e.g., for an initial installation or initial assembly), the risk of cross-threading is significantly reduced. In other embodiments, the top portion 220 is removably coupled with the body 220 via a non-threaded connection, such as, for example, an interference or plugged fit, via one or more gaskets, a slidable connection, etc.

The body 201 and top portion 220 of the humidifier 102, in one embodiment, can be completely or partially made from a rigid plastic material. Examples of a rigid plastic material suitable for use with the humidifier 102 include, but are not limited to, ABS, polyurethane, poly carbonate, PET, and other polymeric materials. Further, in certain implementations, the body 201 is made from a transparent, translucent, or semi-transparent plastic material and includes markings indicating the maximum and/or minimum recommended levels of liquid 119 in the humidifier.

Referring to FIGS. 2 and 3, the top portion 220 includes a fluid refill opening 203 formed in a cover 222 of the top portion 220. In the illustrated embodiment, the cover 222 is a flat, relatively plate-like element that substantially covers the entire open end 105 of the body 201. The fluid refill opening 203 extends through the cover 222 to allow access to the interior 211 of the body 201. As shown, the refill opening 203 is smaller than the open end 105 of the body. However, the fluid refill opening 203 is large enough to accommodate the passage of a relatively high volume (e.g., wide stream) of a refill fluid, such as water. In the illustrated embodiment, the fluid refill opening 203 is about half the size of the open end 105 of the body (i.e., the opening defined by the open end 105 of the body). In other embodiments, the fluid refill opening 203 can be larger than or smaller than about half the size of the open end 105 of the body. The refill opening 203 can have any of various shapes. As illustrated, the refill opening 203 is substantially semi-circular shaped. However, in other embodiments, the refill opening 203 can have other shapes, such as rectangular, square, circular, polygonal, triangular, ovular, etc.

Access through the opening 203 to the interior 211 of the body 201 for refilling the body with water is prevented and allowed by virtue of a lid portion or hatch 204 pivotally coupled to the cover 222. More specifically, the lid portion 204 is pivotable between an closed position in which access through the opening 203 to the interior 211 of the body 201 is prevented (see, e.g., FIG. 2) and an open position in which access through the opening to the interior 211 of the body is allowed (see, e.g., FIG. 3). In the illustrated example, a lid 205 of the lid portion 204 pivots from the closed position downward or inward into the interior or interior space 211 of the body 201 to place the lid portion in the open position as indicated by directional arrow 230. From the open position, the lid 205 pivots upwardly or outward out of the interior space 211 of the body 201 to place the lid portion in the closed position as indicated by directional arrow 232. As the lid 205 pivots upwardly from the closed position, because the area defined by the lip is greater than an area of the opening, a lip 402 around the outer periphery of the lid engages an interior surface of the cover 222 adjacent the fluid refill opening 203 and prevents the lid 205 from opening outwardly away from the interior 211 of the body during use. Stated differently, the engagement between the lip 402 and inner surface of the top portion 220 prevents the buildup of pressure resulting from the flow of oxygen into the body 201 during use from causing the lid 205 to accidentally outwardly open.

To facilitate moving the lid 205 between the open and closing position, the lid portion 204 includes a lever 206 coupled to the lid 205. The lever 206 can be separately formed and attached to the lid 205 or integrally formed as a one-piece monolithic construction with the lid. Generally, the lever 206 extends substantially transversely away from an exterior surface 240 of the lid 205 and rearward of the lid 205. As shown, the lever 206 extends substantially transversely away from the exterior surface 240 and rearward of the lid 205 to form a generally S-shape. In other embodiments, the level 206 can have any of various shapes.

The lever 206 includes a flange or handle 208 at a distal end portion of the lever away from the exterior surface 240. At a first fixed end of the lever 206, the flange 208 extends radially outward from the lever 206 away from a central axis of the container such that at a second free end of the lever 206, a portion of the flange is positioned radially outwardly relative to a radially outward periphery 242 of the fluid refill opening 203. In other words, the flange (and a portion of the lever) is positioned outside a footprint or outer periphery of the lid 205. Basically, when viewed in plan (from the top of the humidifier), a portion of the lever and flange is outside the boundary of the lid. With a portion of the flange 208 positioned radially outwardly relative to the radial outward periphery 242 of the opening 203, the flange contacts an exterior surface of the cover 222 to prevent further inward rotation of the lid 205 beyond the open position. Further, in the open configuration, a substantial (e.g., majority) of the lever is positioned within the interior 211 of the body 201. In one implementation, the entire lever, except the flange, is positioned within the interior 211 of the body.

Additionally, the flange 208 provides an engagement point for a user to open and close the lid. Moreover, because the flange 208 is stopped by exterior surface of the cover 222, the flange remains accessible to close the lid 205 after the body 201 has been filled with a liquid 119, or after a liquid 119 is emptied from the body, such as after use of the humidifier. The lever 206, as depicted, may be formed with a curved configuration to allow the lid 205 to pivot sufficiently inward to allow access to the interior space 211 of the body 201.

Figure 6:
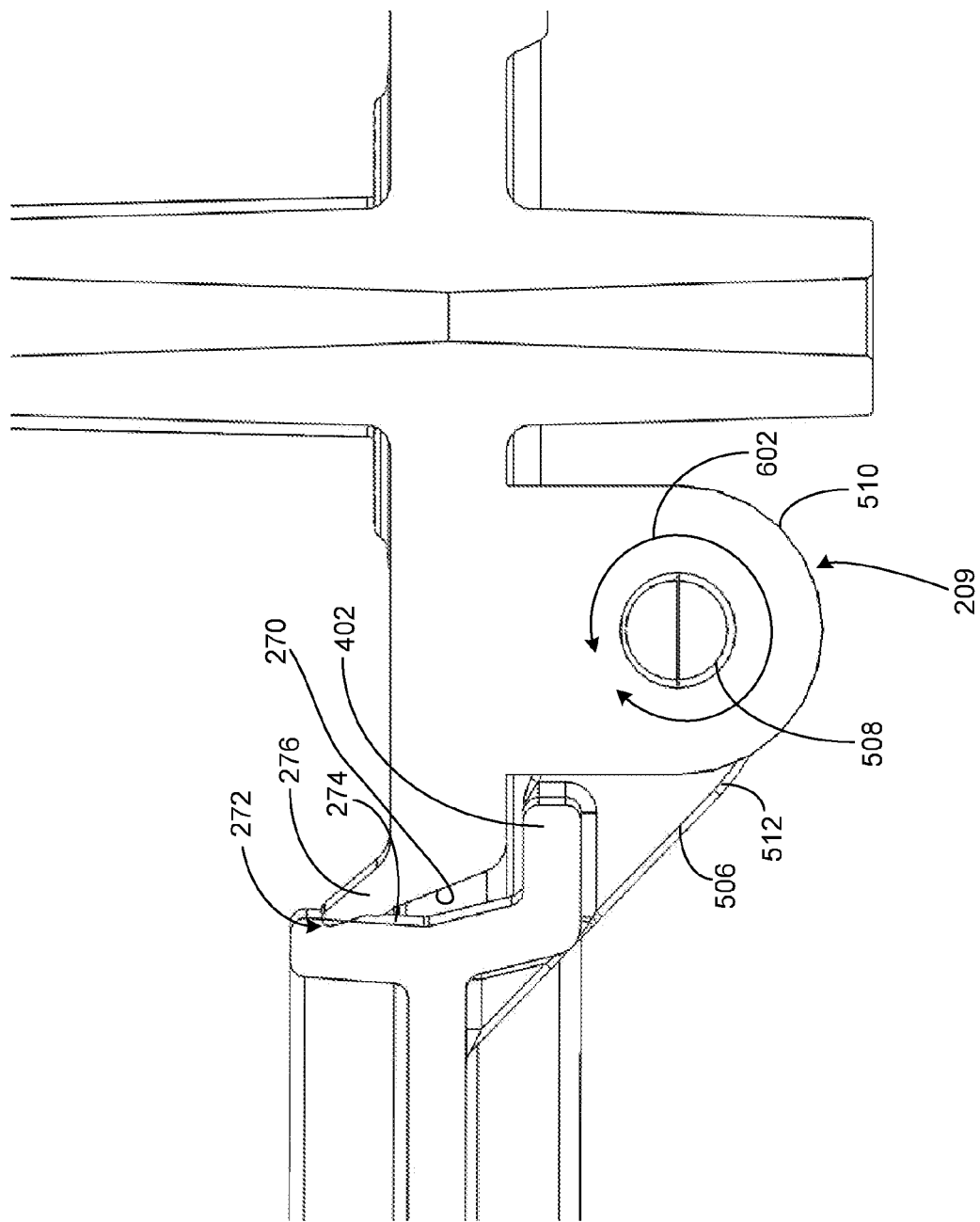
FIG. 6 is a detailed side elevation view of a hinge mechanism pivotally coupling a lid portion to a top portion of an oxygen humidifier according to one embodiment.

Although any of various configurations can be used, the lid portion 204 is pivotally coupled to the cover 222 via a hinge mechanism 209 in the illustrated embodiments. Referring to FIGS. 3 and 6, the hinge mechanism 209 includes a pair of spaced-apart lobes 510 coupled to or formed as part of the cover 222, and a pair of spaced-apart lobes 512 coupled to or formed as part of the lid portion 204. The lobes 510, 512 each include an aperture for receiving a pin or pivot rod 508. The pivot rod 508 couples the lobes 510, 512 together and allows the lobes (as well as the lid portion 204) to rotate or pivot about the pivot rod. To prevent lateral movement of the lobes 512 and lid portion 204 along the pivot rod 508 (i.e., to prevent the lid portion 204 from moving side-to-side during use), the lobes 512 are spaced apart such that both lobes 512 are positionable between and abut the lobes 510 of the cover 222.

As discussed above, the lid 205 pivots inwardly and outwardly about the hinge mechanism 209 to respectively allow and prevent access to the interior space 211 of the body 201 of the humidifier 102. Access to the interior space 211, as well as the release of oxygen and fluid within the interior space 211 through the opening 203, is prevented when the lid 205 is in the closed position. Several alternative embodiments are configured to promote a seal between the lid 205 and the opening 203 (e.g., the surface 270 of the cover 222 defining the opening 203) and to maintain the seal during use. Beneficially, such embodiments do not require the use of a spring or similar extraneous biasing member to maintain the lid portion in the closed configuration.

In one embodiment, the seal between the lid 205 and opening 203 is created and maintained via an interference fit 272 between a peripheral ridge 274 and the surface 270 of the cover 222 defining the opening 203 as shown in FIG. 6. The ridge 274 extends substantially transversely from the lid 205, and in some implementations may be slightly radially outwardly angled away from a center of the lid. The surface 270 of the cover 222 is defined at least partially by a radially inwardly angled lip 276 extending about a periphery of the opening 203. The lip 276 is inwardly angled because it is angled inwardly toward a center of the opening. The inward angle of the lip 276 facilitates engagement with the ridge and a smooth transition into the interference fit 272. Moreover, the lip 276 is relatively thin and resiliently deformable compared to the thickness of the other portions of the lid 205.

The outer periphery of the ridge 274 and inner periphery of the lip 276 define the same shape. However, the outer peripheral shape defined by the ridge 274 is sized to be slightly larger than the inner peripheral shape of the lip 276. Accordingly, as the lid 204 is rotated clockwise according to the directional arrows 602, the ridge 274 comes into contact with the lip 276 with the lip resisting further rotation of the lid. However, as the rotational force applied to the lid 204 (e.g., via the lever 206 and flange 208) exceeds the modulus of elasticity of the lip 276, the lip slightly deforms to create the interference fit 272. Because the lip 276 is resiliently deformable, it applies a pressure against the ridge 274 at the location of the interference fit 272 to effectively create a seal between the lip and ridge (i.e., between the cover 222 and lid 204). Moreover, the pressure applied against the ridge 274 by the lip 276 also frictionally maintains (e.g., via a press-fit) the lid 204 in place relative to the cover 222 to effectively lock the lid in the closed position. To open the lid 204 from the closed position, a user can apply a rotational force (e.g., a counterclockwise directed force according to directional arrows 602) that overcomes the frictional force between the lip 276 and ridge 274. As the frictional force is overcome, the lip 276 returns to its original size and shape.

Figure 5A:
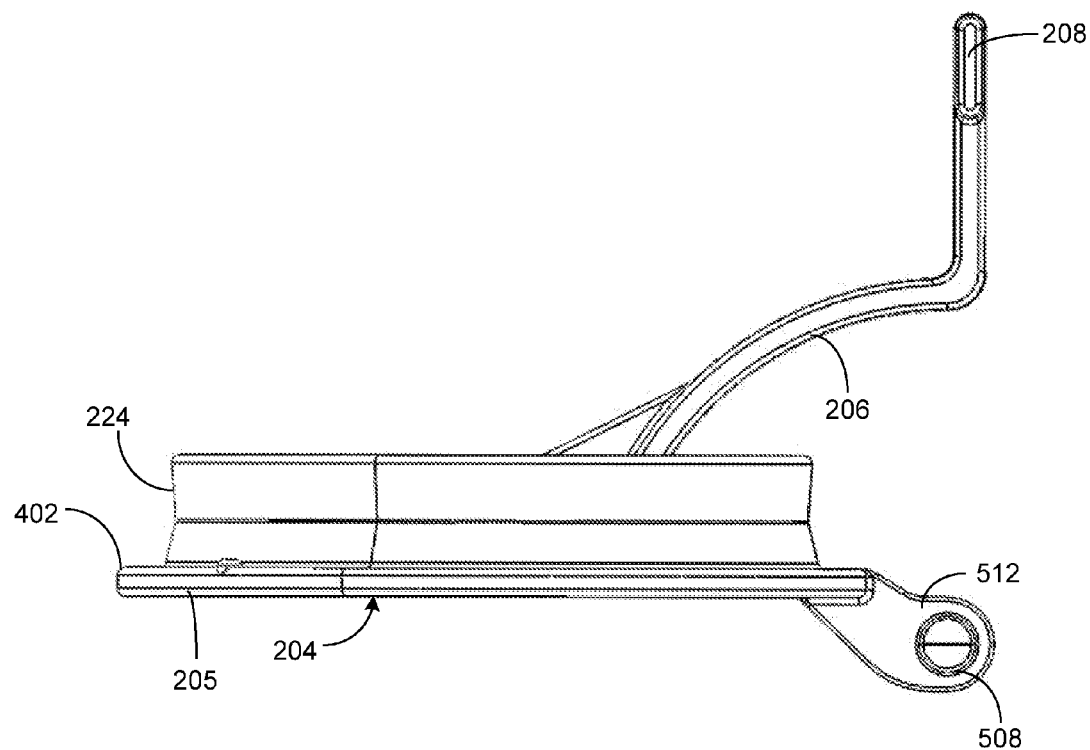
FIG. 5A is a side elevation view of the lid portion of FIG. 4.
Figure 5B:
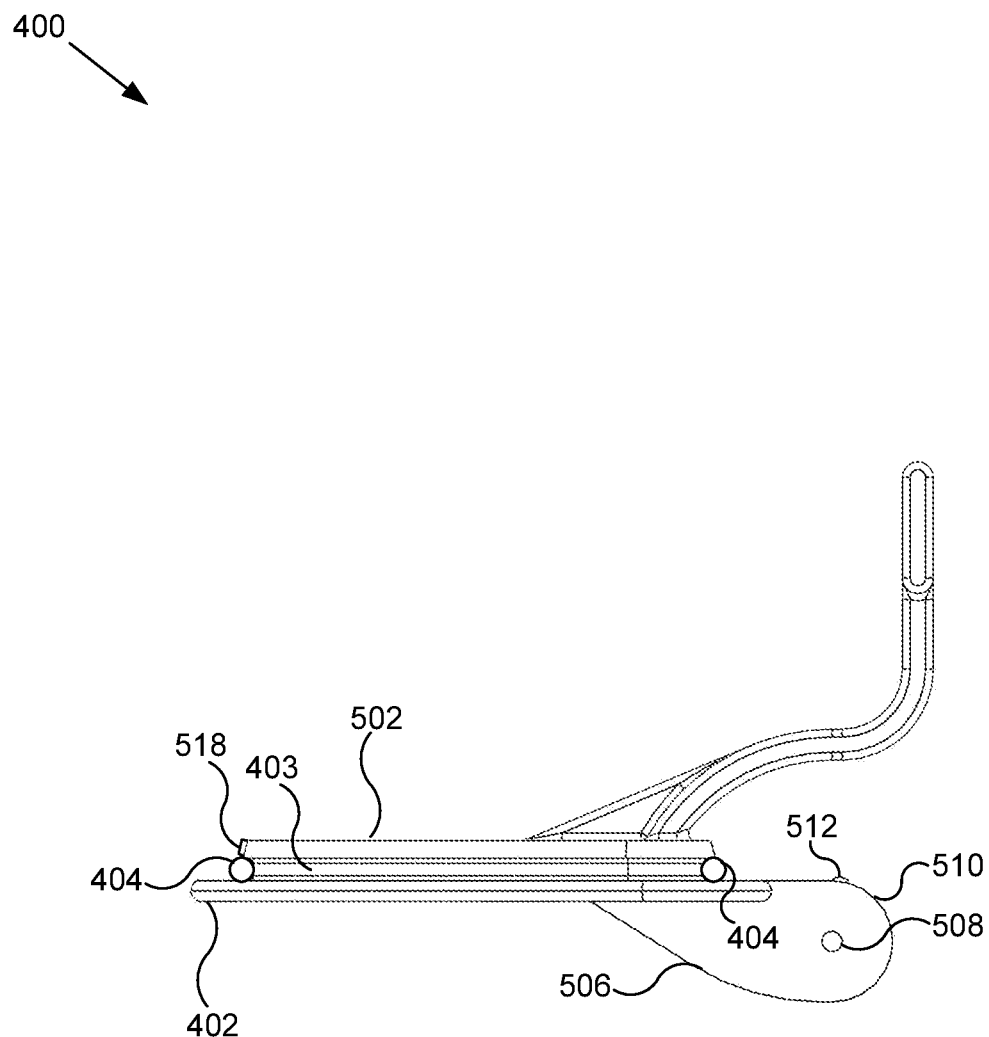
FIG. 5B is a side elevation view of a lid portion according to another embodiment.

In an alternative embodiment, in addition or alternative to an interference fit coupling, the seal between the lid 205 and opening 203 can be created and maintained via an deformable gasket coupling. As shown in FIG. 5B, the lid 205 of the lid portion 204 includes a recess 403 formed about a ridge 502. The recess 403 is configured to receive a flexible gasket 404. When in the closed position, the flexible gasket 404 sealingly engages the surface defining the opening 203 to seal the opening 203.

Moreover, in some embodiments, maintaining a sealing engagement between the lid 205 and opening 203 (i.e., locking the lid 205 in the closed position) is facilitated via one or more detents 512, 518 coupled to or formed with a lid portion 400 (see, e.g., FIG. 5B). The detents 512, 518 can be configured to engage corresponding detents formed in the cover 222. As shown, the detent 512 is formed on the lobe 510 and the detent 518 is formed on a ridge 502 of the lid 205. The detent 518 may be positioned as depicted, substantially centered with reference to the lid 205. Alternatively, the detent 518 may be positioned anywhere along the ridge of the lid 205. Furthermore, multiple detents 510, 518 may be provided and positioned along the ridge of the lid 205 or lobe.

The detents 512, 518 are configured to engage the corresponding detents or catches formed in the cover 222 to prevent relative rotation between the lid and cover. Generally, a force is required to move the detents past the corresponding catches to place the lid in the closed position, and a force directed in an opposite direction is required to again move the detents past the corresponding catches to take the lid out of the closed position. In other words, the lid will not release or open until the patient or caretaker supplies a force sufficient to overcome the engagement between the detents and the corresponding catches. As used herein, the term "detent" refers to any mechanism that mechanically resists the rotation or pivoting of the attachment mechanism 506.

The lid portion 204, in one embodiment, is formed of a rigid polymer material. The material may be substantially equivalent to the material used to form the humidifier 102 and the top portion 220 of FIGS. 1-3.

As described above, the humidifier 102 includes inlet and outlet ports 104, 106. The inlet and outlet ports 104, 106 may be integrally formed with the cap 222 of the top portion 220, or alternatively formed separately and attached to the cap 222. In either embodiment, the inlet and outlet ports 104, 106 are sealably coupled with the cap 222 of the top portion 220 so that fluid and liquid does not leak from the humidifier 102. The inlet and outlet ports 104, 106 include external engagement portions that extend substantially transversely away from the exterior surface of the cap 222. The ports 104, 106 are configured to receive and retain a respect one of a fluid inflow and outflow tube. The inlet and outlet ports 104, 106, while depicted as substantially circular, may be shaped and formed according to the tube that will connect to the ports 104, 106. Although not shown, the inlet port 104 also includes an internal engagement portion that extends substantially transversely away from the interior surface of the cap 222 such that the internal engagement portion is positioned substantially within an internal cavity of the body 201. The internal engagement portion is configured to receive and retain a diffuser tube as will be described in more detail below. The inlet port 104 defines a channel through which dry oxygen in the fluid inflow tube is directed into the diffuser tube.

The top portion 220 also includes a pop-up pressure release valve 210. The pressure release valve 210 may be press-fit into the top portion 220, or otherwise coupled with the top portion 220 so that the fluid 119 does not leak from the humidifier 102 through the pressure release valve. The pressure release valve 210 is movable within an aperture formed in the cover 222. Although not shown, a biasing member or other biasing technique is utilized to bias the valve 210 in a closed position, which prevents oxygen in the body from escaping the body. However, when the pressure inside the humidifier 102 exceeds a pre-determined value associated with the biasing force of the biasing member, the pressure release valve 210 will open (e.g., pop-up or move upwardly within the aperture in the cover). In one embodiment, when opened, the pressure release valve 210 will notify the patient 110 or caretaker that excessive pressure has been reached. Additionally, or alternatively, when opened, the pressure release valve will release oxygen from the body until the pressure within the body 201 drops to an acceptable level. As oxygen is released, and the pressure within the body drops, the valve 210 will correspondingly lower from an open position into the closed position. For embodiments where the valve 210 provides notification, the notification may be either visual or aural. In one implementation, the pressure release valve 210 makes a whistle sound when the pressure inside the humidifier 102 is greater than the pre-determined value. In the same or another implementation, the portion of the pop-up valve 210 below the external surface of the cover 222 may have a color that is different than the top portion 220. Accordingly, when the valve 210 is actuated or pops up, a user receives a clear visual indication that the valve 210 is open by recognizing the different color being visible.

Figure 7:
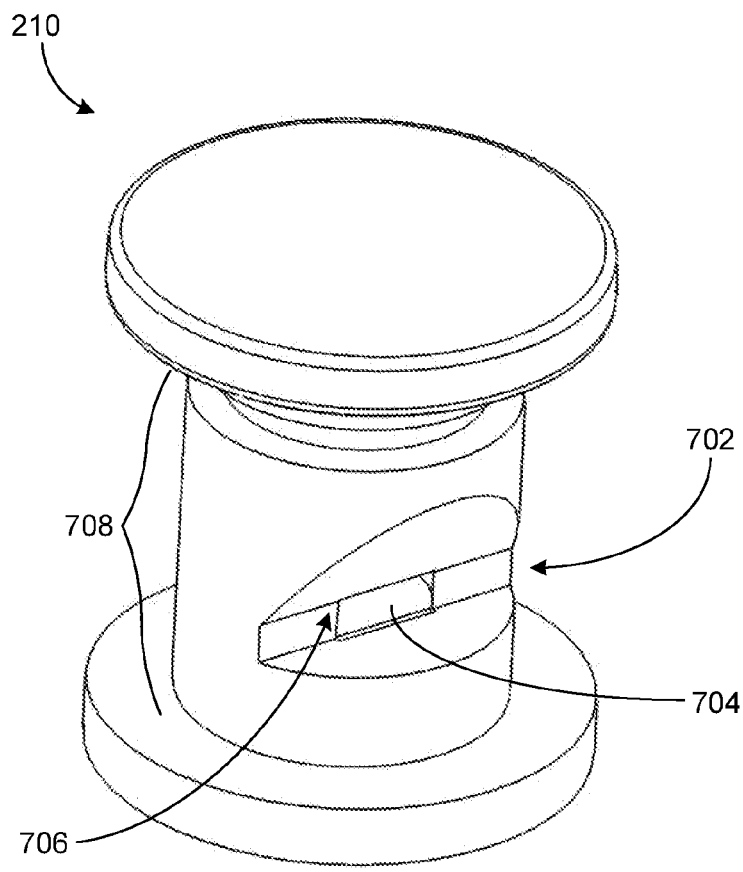
FIG. 7 is a top perspective view of a pressure release valve of an oxygen humidifier according to one embodiment.

As shown in FIG. 7, in one embodiment, the pressure release valve 210 is a whistle assembly 702. As discussed above, the pressure release valve 210 may be press-fit into the cover 220 such that the pressure release valve 210 forms a seal with the top portion 220 until a pre-determined interior pressure is reached, at which point the pressure release valve 210 releases the pressure and/or notifies the patient 110 or caretaker of the excessive pressure. In one example, the whistle assembly 702 is formed with a channel 704 that extends into the interior area of the humidifier and a fipple 706 that splits the flow of air from the humidifier to create a turbulent vortex which causes air to vibrate and subsequently produce an audible alert. In addition, or alternatively, the pressure release valve 210 may be colored with a color indicative of a warning to visually warn a person of the excessive pressure. For example, the portion 708 may be colored a bright red or yellow color.

As discussed generally above, the pressure release valve 210 is configured to remain in a closed configuration (where oxygen is not allowed to flow through the channel 704) until a pre-determined pressure is reached inside the humidifier 102. In one embodiment, the pre-determined pressure is in the range of between about 2 and 12 psi. In a further embodiment, the pre-determined pressure is in the range of between about 3 and 8 psi.

Figure 8:
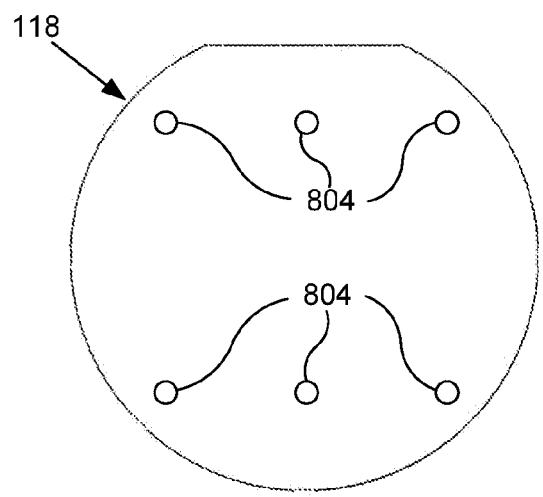
FIG. 8 is a side elevation view of a diffuser of an oxygen humidifier according to one embodiment.
Figure 9:
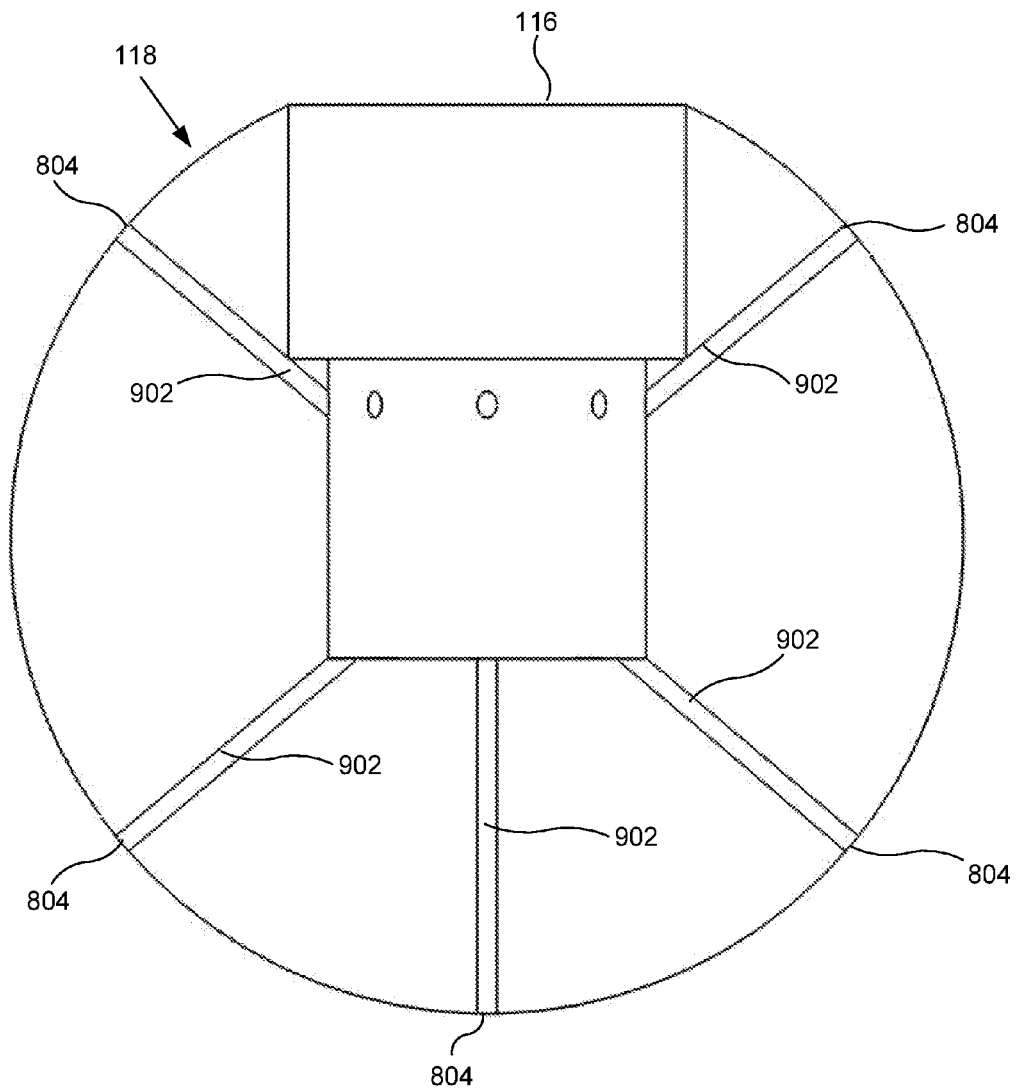
FIG. 9 is a cross-sectional side elevation view of a diffuser of an oxygen humidifier according to one embodiment.

Referring to FIGS. 8 and 9, one embodiment of the diffuser 118 is shown. As used herein, the term "diffuser" refers to a device that aerates the oxygen flow into a liquid. The diffuser 118, as depicted, is formed as a generally sphere-shaped element with multiple openings 804 spaced radially about the perimeter of the diffuser 118. The openings 804 are fluidly connected with the fluid conduit 116 described above with reference to FIGS. 1-3 to receive and expel fluid 112 flowing through the fluid conduit. The size of the openings is determined according to a desired bubble size. In one example, the openings have a diameter in the range of between about 0.5 and 8 mm. In certain embodiments, the diffuser 118 is spherical to facilitate distribution or expulsion of the incoming oxygen flow 112 into the liquid 119. Alternatively, the diffuser 118 may be formed of other shapes, including, but not limited to, squares, rectangles, ellipses, cones, triangles, etc. The angles at which the openings 804 expel fluid into the liquid 119 can vary. In certain embodiments, the angles of all the openings are greater than or less than an angle perpendicular to the sides of the body 201 (i.e., parallel to the bottom surface of the body). In other words, in certain embodiments, the diffuser 118 is configured to expel fluid 112 into the liquid 119 at any of various angles other than perpendicular to the sides of the body. Angling the openings 804 in this manner reduces the buildup of bubbles on the sides of the body.

The diffuser 118 includes multiple openings 804 connected fluidly to the conduit 116. The openings 804 are fluidly coupled with the conduit 116 by a plurality of channels 902. Each opening 804 is connected to a channel 902 that connects to the conduit 116. In one embodiment, the channels 902 direct oxygen 112 to the openings 804 that in turn aerate the liquid 119. Each channel extends from the conduit 116 to an opening 804 in a direction that is not perpendicular to a side wall (or parallel to a bottom surface) of the container 102 of FIG. 1. In the depicted embodiment, the channels 902 extend either parallel to the side wall of the body of the humidifier, or at a 45-degree angle relative to the side wall of the container, for example. The angle relative to the side wall of the container is selected to maximize the aerating effect of the diffuser 118, and may be in the range of between about 0 degrees (parallel) and 85 degrees. In other words, many angles are suitable for use with the diffuser 118.

Figure 10:
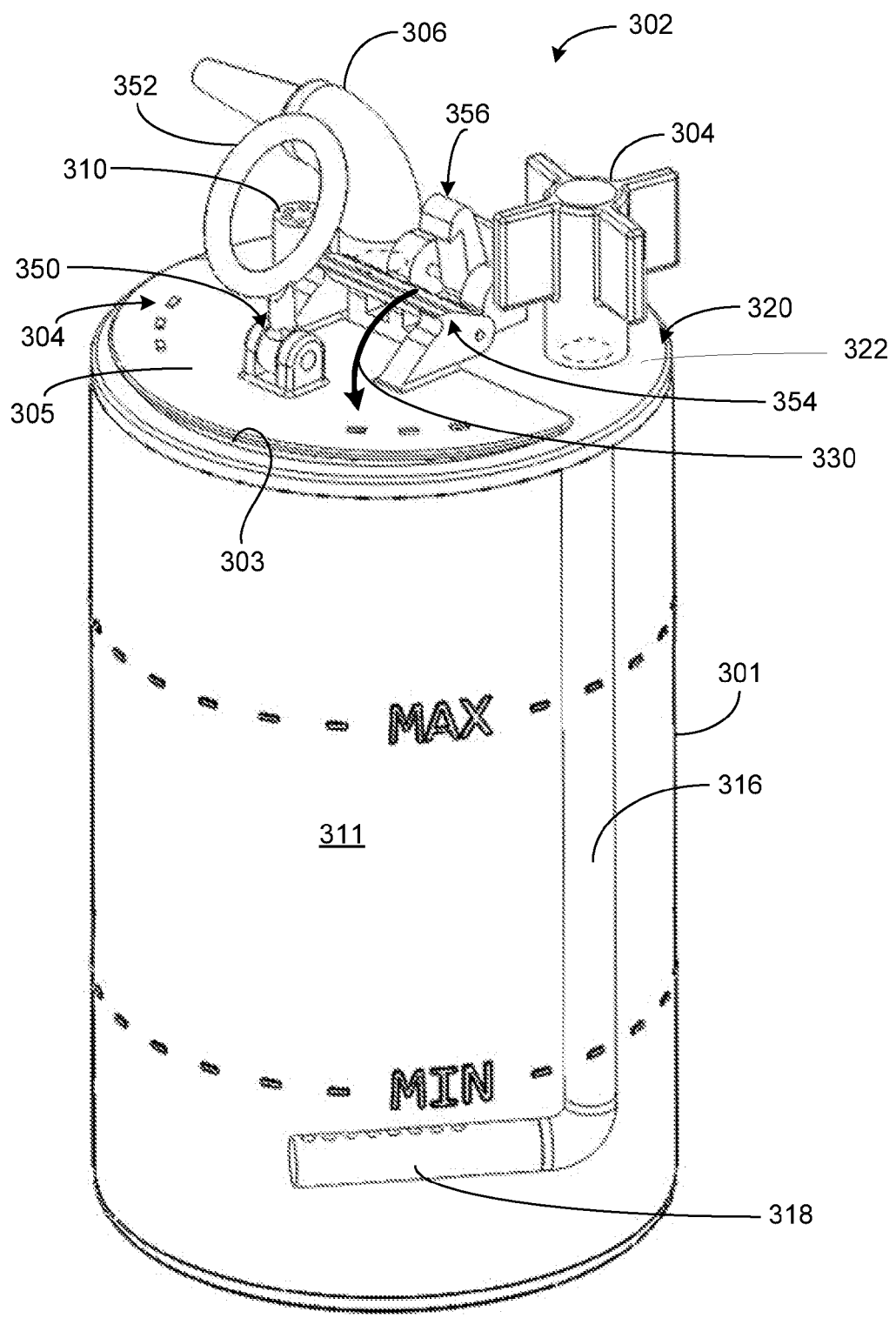
FIG. 10 is a top perspective view of an oxygen humidifier shown with a transparent container and a lid portion in a closed configuration according to yet another embodiment.
Figure 11:
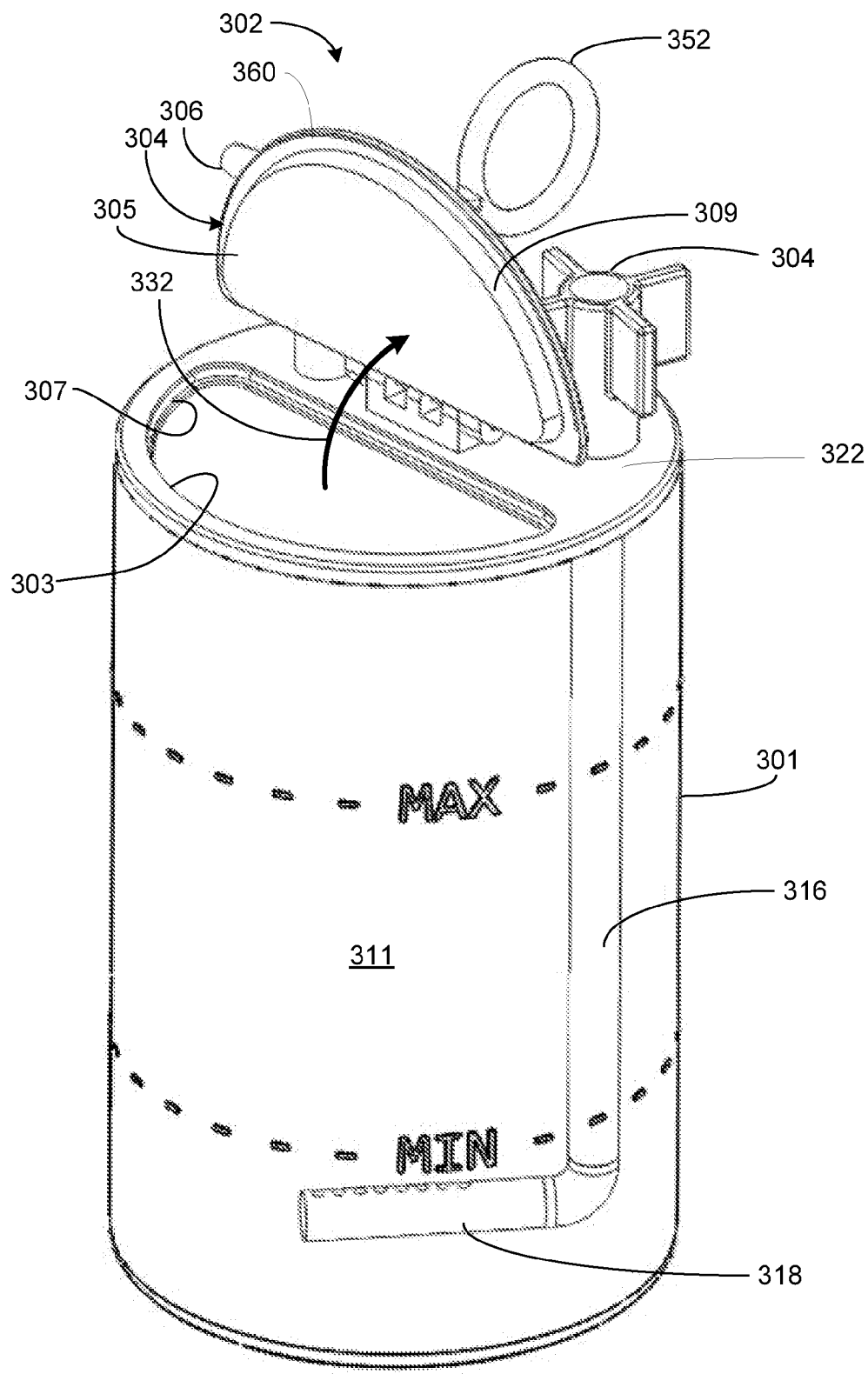
FIG. 11 is a top perspective view of the oxygen humidifier of FIG. 10 but shown with the lid portion in an open configuration.
Figure 12:
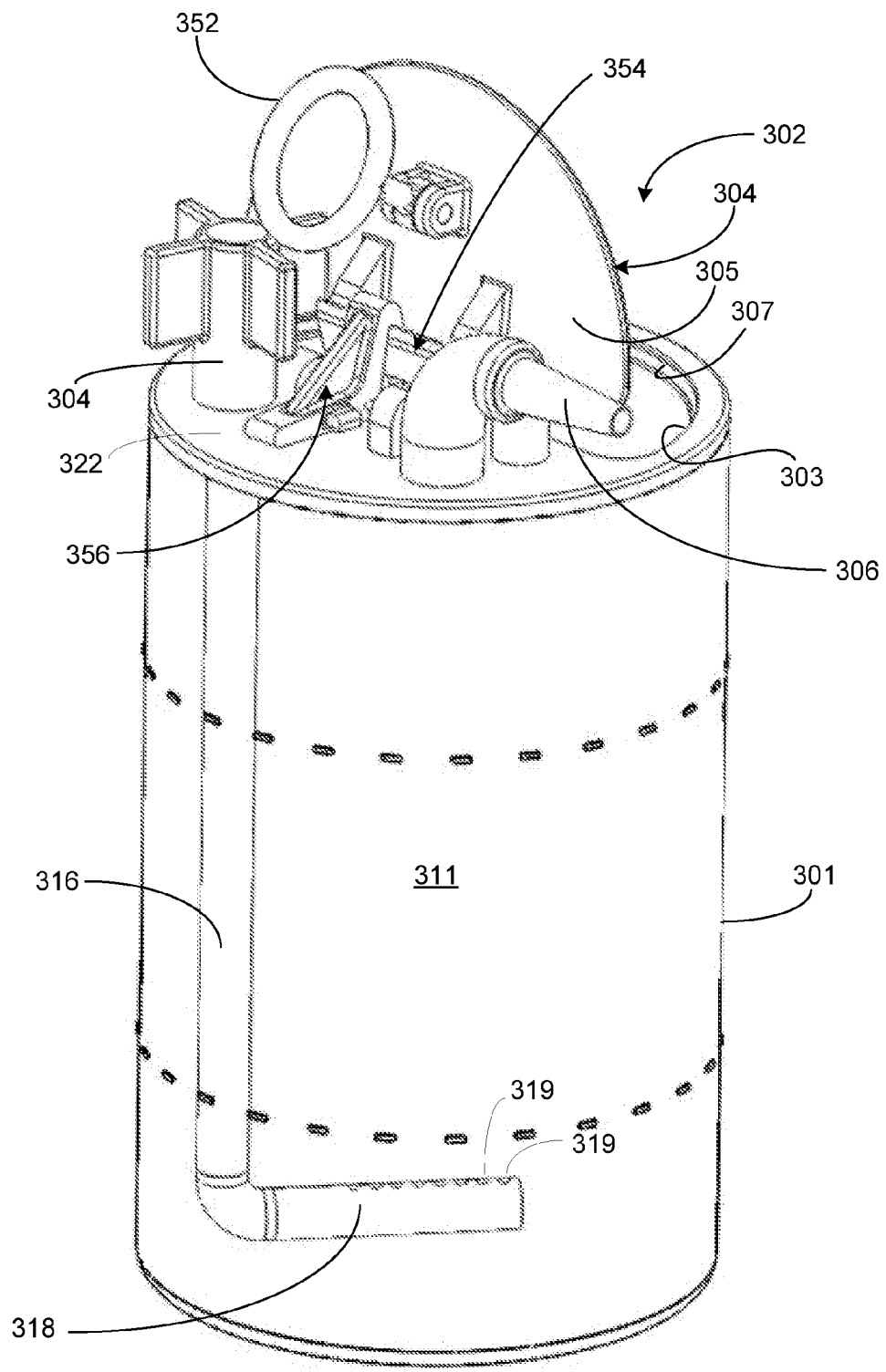
FIG. 12 is a rearward perspective view of the oxygen humidifier of FIG. 10 shown with the lid portion in the open configuration.

Referring to FIGS. 10-12, another embodiment of an oxygen humidifier 302 is shown. The oxygen humidifier 302 includes features analogous to the features of the oxygen humidifier 102, with like numbers referring to like elements. However, the oxygen humidifier also includes some differences, which will be described in more detail below. Unless otherwise noted below, the oxygen humidifier 302 shares the same features as the oxygen humidifier 102, and as such, the description of the features of the oxygen humidifier 102 provided above applies equally to the oxygen humidifier 302.

Similar to the oxygen humidifier 102, the oxygen humidifier 302 includes a top portion 320 with a fluid refill opening 303 formed in a cover 322 of the top portion 320. However, access through the opening 303 is prevented and allowed by a lid portion or hatch 304 that is configured to open, close, and seal in a manner different than the lid portion 204 of the oxygen humidifier 102. Generally, as opposed to opening inwardly into an interior 311 of the container 301 to switch from a closed configuration to an open configuration, the lid portion 304 of the oxygen humidifier 302 opens outwardly away from the interior 311 of the container 301 to switch from the closed configuration and to the open configuration. In other words, in the open configuration, the lid 305 of the lid portion 304 is positioned externally relative to the interior 311 of the container, as opposed to being positioned within or internally relative to the interior. Similarly, the lid 305 is rotated inwardly toward the interior 311 to switch from the open configuration to the closed configuration.

To facilitate moving the lid 305 between the open and closing position, the lid portion 304 includes a handle 350 coupled to an external surface of the lid 305. The handle 350 may include a user gripping portion 352, which can be a ring that is movably coupled to the lid 305. The user gripping portion 352 can be coupled to the lid 305 via a swivel, pivot, and/or ball-and-socket connections, among other types of connections. A user may grip the user gripping portion 352 and pull the handle 350 in a direction indicated by directional arrow 332 (see FIG. 11) to open the lid 305 from the closed configuration as shown in FIG. 10. Similarly, a user may grip the user griping portion 352 and push the handle 350 in an opposite direction indicated by directional arrow 330 (see FIG. 10). The handle 350 can be separately formed and attached to the lid 205 or integrally formed as a one-piece monolithic construction with the lid.

Referring to FIG. 11, the lid 305 includes a lip 360 extending about an outer periphery of the lid. The lip 360 is sized to be larger than the opening 303 such that as the lid 305 is rotated inwardly from the open configuration, the lip 360 contacts an exterior surface of the cover 322 to prevent further inward rotation of the lid and position the lid in the closed configuration. A gasket 307 may be used to promote fluid sealing engagement between the lid 305 and the opening 303 when the lid is in the closed configuration. In the illustrated embodiment, the gasket 307 is seated in a recess formed in the cover 322 about the periphery of the opening 303. In the closed configuration, the gasket 307 sealingly engages a ridge 309 formed in an interior surface of the lid 305 to create the sealed connection between the lid and the opening. In alternative embodiments, the gasket 307 is seated in a recess formed in the lid 305 with the gasket engaging a surface of the cover 322 defining the opening 303 to create the seal. In yet other embodiments, no gasket is used and the seal between the lid 305 and opening 303 is created via an interference fit or press-fit between the ridge 309 and the surface of the cover 322 defining the opening 303.

The lid 305 is pivotally coupled to the top portion 320 via a hinge connection. Separate from or integrated with the hinge connection is a cam element 354 fixedly coupled to the lid 305. The cam element 354 rotates with the lid 305 as the lid is rotated between closed and open configurations. In this manner, the cam element 354 can be defined as a rotating cam. The cam element 354 includes a toothed portion configured to engage and disengage with the notched portion of a latch element 356. The latch element 356 is fixedly coupled to the cover 322 of the top portion 320, and is at least partially resiliently flexible. As the lid 305 is rotated from the closed configuration into the open configuration, the cam element 354 contacts and flexes the latch element 356. Further rotation causes the latch element 356 to flex until the toothed portion of the cam element 354 snaps into engagement with the notched portion of the latch element 356. In this configuration, engagement between the cam element 354 and latch element 354 removably or releasably locks the lid 305 in place in the open configuration for refilling or cleaning the container 301.

After refilling or cleaning, or otherwise when closing of the lid 305 is desired, a user can engage the handle 350 and/or lid and push the lid in the direction 330 with a pushing force that overcomes the engagement force between the cam element 354 and latch element 356. Such a force causes the latch element 356 to deform to allow the cam element 354 to disengage with the latch element. Once the cam element 354 is disengaged with the latch element 356, the lid 305 can be rotated into the closed configuration. In the same or alternative embodiments, the user can directly engage (e.g., pull back on) the latch element 356 to deform the latch element and allow disengagement between the cam element 354 and latch element. It is recognized that other techniques and connections can be utilized to releasably lock or contain the lid 305 in the open configuration.

The oxygen humidifier 302 also includes a diffuser 318. However, the diffuser 318 includes a tube that extends transversely away from and is fluidly coupled with the fluid conduit 316. Generally, the fluid conduit 316 is substantially parallel with a central axis of the container 301 and the diffuser 318 is substantially perpendicular relative to the central axis of the container. The diffuser 318 includes a plurality of openings 319 through which dry oxygen diffuses into the fluid contained in the container 301. The openings 316 can face (i.e., be open in) an upward direction toward the top portion 320 that is substantially parallel to the central axis of the container 301.

Although not shown, in some embodiments, an oxygen humidifier of the present disclosure includes a top portion that is permanently coupled with the container, and a lid that is slidable along a plane substantially parallel to the cover of the top portion between an open configuration and closed configuration to respectively allow and block access to an opening formed in the top portion.

The present subject matter may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An oxygen humidifier, comprising:
 a container defining an interior space;
 a top portion permanently coupled to the container, the top portion comprising an opening for accessing the interior space of the container;
 a lid portion movably coupled to the top portion, the lid portion being configured to move between a closed configuration and an open configuration, wherein in the closed configuration the lid portion seals the opening and in the open configuration the lid portion allows access to the interior space through the opening; and
 an oxygen diffuser positioned within the interior space;
 wherein the lid portion is rotatably coupled to the top portion, the lid portion being configured to rotate between the closed configuration and the open configuration, wherein in the open configuration the lid portion is positioned within the interior space of the container.

2. The oxygen humidifier of claim 1, further comprising an oxygen inlet port formed in the top portion and a fluid conduit fluidly connected with the oxygen inlet port, wherein the fluid conduit extends into the interior area of the container, the apparatus further comprising an oxygen outlet port formed in the top portion.

3. The oxygen humidifier of claim 2, wherein the diffuser is fluidly coupled with an end of the fluid conduit, the diffuser being configured to diffuse an oxygen flow into a liquid retained within the container.

4. The oxygen humidifier of claim 3, wherein the fluid conduit and diffuser are positioned off-center within the interior of the container relative to a central axis of the container.

5. The oxygen humidifier of claim 1, further comprising a pressure release valve coupled with the top portion, the pressure release valve being configured to provide at least one of a visual and an aural notification when pressure inside the container has reached a predetermined pressure.

6. The oxygen humidifier of claim 1, further comprising a lever coupled to and extending outward from the lid portion, wherein a flange portion of the lever extends outwardly beyond an outer periphery of the opening.

7. The oxygen humidifier of claim 6, wherein the flange portion of the lever contacts an outer surface of the top portion when the lid portion has moved to the open configuration to prevent further movement of the lid portion in an opening direction.

8. The oxygen humidifier of claim 6, wherein the lid portion is movable by engaging the flange portion of the lever.

9. The oxygen humidifier of claim 6, wherein in the open configuration a substantial portion of the lever is positioned within the interior space of the container.

10. The oxygen humidifier of claim 1, wherein the diffuser is substantially spherical shaped, the diffuser comprising a plurality of openings through which oxygen is diffusible.

11. The oxygen humidifier of claim 10, wherein the plurality of openings open in directions substantially non-perpendicular relative to a sidewall of the container.

12. The oxygen humidifier of claim 1, wherein the lid portion is releasably retained in the closed configuration via an interference fit between the lid portion and the top portion.

13. The oxygen humidifier of claim 12, wherein the top portion comprises a lip defining the opening, the lip being inwardly angled relative to a center of the opening, and wherein the lid portion comprises a ridge, an outer periphery of the ridge being greater than an inner periphery of the lip.

14. The oxygen humidifier of claim 1, wherein the lid portion is releasably retained in the closed configuration via a detent mechanism.

15. The oxygen humidifier of claim 1, wherein at least one of the top portion and lid portion comprises a flexible gasket, and wherein in the closed configuration, the flexible gasket seals the opening.

16. The oxygen humidifier of claim 1, wherein the lid portion comprises a lip defining an area greater than an area of the opening, the lip being contactable with an interior surface of the top portion to prevent upward rotation of the lid portion relative to the top portion beyond a position associated with the closed configuration.

17. The oxygen humidifier of claim 1, wherein the lid portion is releasably retained in the open configuration via engagement between a cam element coupled to the lid portion and a latch element coupled to the top portion.

18. An oxygen humidifier, comprising:
   a container defining an interior space for storing a fluid, the container comprising an open end;
   a top portion coupled to the open end, the top portion comprising an opening smaller than the open end of the container, wherein the interior space is accessible through the opening in the top portion, the top portion further comprising an oxygen inlet port and an oxygen outlet port; and
   a lid portion rotatably coupled to the top portion, the lid portion comprising a lid and a lever coupled to the lid, wherein the lid seals the opening via an interference fit in a closed position and is positioned within the interior space of the container to allow access to the interior space through the opening in the top portion in an open position, the lid being rotatable between the closed and open positions via actuation of the lever.

19. A method for humidifying oxygen, comprising:
   directing dry oxygen into an oxygen humidifier, the oxygen humidifier comprising a container defining an interior space, a top portion permanently coupled to an open end of the container, and an oxygen diffuser positioned within the interior space, wherein the top portion comprises an opening through which the interior space of the container is accessible, the top portion further comprising a lid rotatably coupled to the top portion, the lid being configured to move between a closed configuration and an open configuration, wherein in the closed configuration the lid seals the opening and in the open configuration the lid allows access to the interior space through the opening, wherein the lid comprises a handle extending from the lid;
   rotating the lid in a first direction to position the lid within the interior of the container and out of sealing engagement with the opening via actuation of the handle;
   preventing rotation of the lid in the first direction beyond a fully open position;
   with the lid positioned out of sealing engagement with the opening, passing a fluid through the opening and into the container;
   rotating the lid in a second direction opposite the first direction to position the lid into sealing engagement with the opening via actuation of the handle; and
   directing humidified oxygen from the oxygen humidifier.

* * * * *